United States Patent
Ganion et al.

(10) Patent No.: US 8,078,285 B2
(45) Date of Patent: Dec. 13, 2011

(54) REVERSIBLE IMPLANTABLE ACOUSTIC SENSOR

(75) Inventors: Vincent P. Ganion, Andover, MN (US); David A. Anderson, Stanchfield, MN (US); Lewis J. Werner, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 929 days.

(21) Appl. No.: 12/057,629

(22) Filed: Mar. 28, 2008

(65) Prior Publication Data
US 2009/0248114 A1    Oct. 1, 2009

(51) Int. Cl.
*A61N 1/00* (2006.01)

(52) U.S. Cl. ........................................................ 607/60

(58) Field of Classification Search ................ 607/9, 27, 607/62, 17–20; 600/300
See application file for complete search history.

(56) References Cited

U.S. PATENT DOCUMENTS

| | | | |
|---|---|---|---|
| 4,481,950 A * | 11/1984 | Duggan ............................ 607/29 |
| 4,770,185 A | 9/1988 | Silverstein et al. |
| 5,757,104 A * | 5/1998 | Getman et al. ................. 310/317 |
| 6,082,367 A | 7/2000 | Greeninger et al. |
| 6,247,474 B1 | 6/2001 | Greeninger et al. |
| 6,354,299 B1 | 3/2002 | Fischell et al. |
| 6,477,406 B1 | 11/2002 | Turcott |
| 6,527,729 B1 | 3/2003 | Turcott |
| 6,869,404 B2 | 3/2005 | Schulhauser et al. |
| 7,035,684 B2 | 4/2006 | Lee |
| 7,570,998 B2 * | 8/2009 | Zhang et al. ..................... 607/18 |
| 7,580,750 B2 * | 8/2009 | Doron et al. ..................... 607/36 |
| 2002/0099412 A1 | 7/2002 | Fischell et al. |
| 2003/0004403 A1 | 1/2003 | Drinan et al. |
| 2006/0009818 A1 | 1/2006 | von Arx et al. |
| 2007/0055308 A1 | 3/2007 | Haller et al. |

FOREIGN PATENT DOCUMENTS
EP   1596629   11/2005
WO   2006033104   3/2006

OTHER PUBLICATIONS

International Search Report, US2009/038730, 4 pages.

* cited by examiner

*Primary Examiner* — George Evanisko
*Assistant Examiner* — Mallika Fairchild
(74) *Attorney, Agent, or Firm* — Michael C. Soldner

(57) ABSTRACT

An implantable medical device having an acoustic element includes a control module coupled to the acoustic element, an acoustic sensing module coupled to the control module, and a patient alert driver module coupled to the control circuit. The patient alert driver module generates a patient alert drive signal for activating the acoustic element to emit a patient alert signal. The control module includes an isolation circuit for isolating the acoustic sensing module from the acoustic element in response to the patient alert drive signal.

8 Claims, 4 Drawing Sheets

US 8,078,285 B2

REVERSIBLE IMPLANTABLE ACOUSTIC SENSOR

TECHNICAL FIELD

The invention relates generally to implantable medical devices and, in particular, to acoustical sensing and acoustical patient alert signal generation using a common acoustic element.

BACKGROUND

Implantable medical devices (IMDs) often rely on sensors to detect physiological signals for monitoring a patient condition and/or determining a need for delivering a therapy. Acoustic sensors are one type of sensor that may be used to detect physiological signals within the body. For example, heart sounds detected by acoustic sensors are useful in detecting abnormal heart function. Other physiological signals that may be sensed using acoustic sensors include intestinal sounds and lung sounds.

Some IMDs are capable of generating a patient alert signal to notify the patient of a condition requiring medical attention or a response by the patient. A patient alert condition may be related to the function or status of the IMD itself or a physiological condition detected by the IMD. A patient alert signal may be an audible signal emitted by an acoustic element.

An acoustic element, such as a piezoelectric transducer, used for emitting a patient alert signal is typically activated using a high frequency signal, for example on the order of 800 to 1,200 Hz. Acoustic signals sensed for detecting heart sounds may have a frequency of about 15 Hz to 400 Hz. For at least this reason, a circuit for generating an acoustical patient alert and a circuit for sensing acoustic signals each have different operational requirements. As such, such acoustical patient alert and acoustical sensing circuits have been implemented separately using separate acoustic elements.

DETAILED DESCRIPTION

Figure 1:
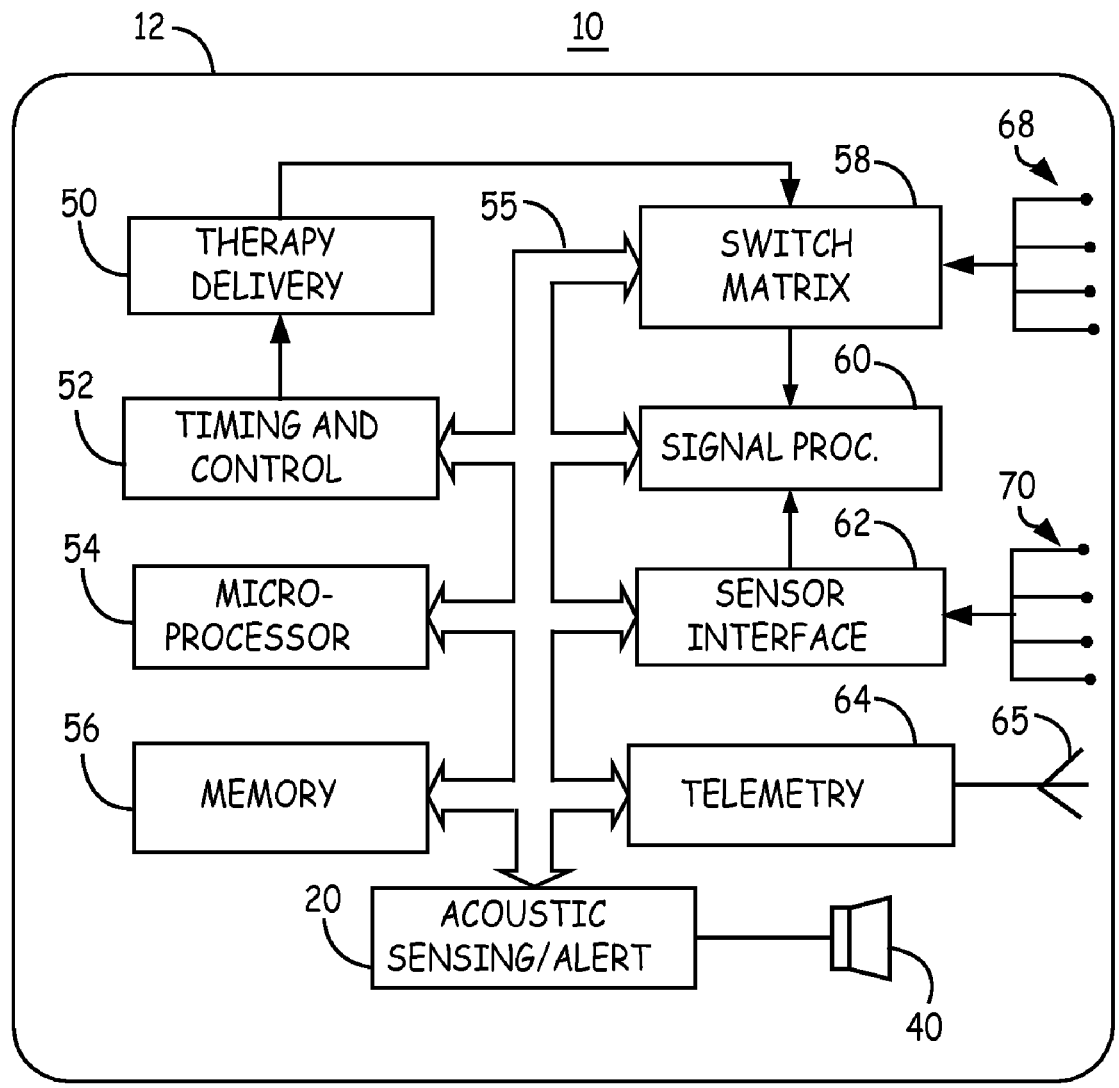
FIG. 1 is a functional block diagram of one embodiment of an IMD capable of generating an acoustical patient alert and sensing acoustical signals using a common acoustic element.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of one embodiment of an IMD capable of generating an acoustical patient alert and sensing acoustical signals using a common acoustic element. IMD 10 may be embodied as a variety of implantable devices, including but not limited to a cardiac pacemaker, cardioverter defibrillator, drug pump, neurological stimulator or the like. IMD 10 may be implemented as a monitoring device for receiving and processing physiological signals for use in diagnosing or monitoring a patient condition or disease. Alternatively, IMD 10 may be a therapeutic device having therapy delivery capabilities in addition to sensing capabilities.

IMD 10 includes a hermetic housing 12 to enclose circuitry within the IMD 10. IMD 10 generally includes timing and control circuitry 52 and an operating system that may employ microprocessor 54 or a digital state machine for timing sensing and therapy delivery functions in accordance with a programmed IMD operating mode. Microprocessor 54 and associated memory 56 are coupled to the various components of IMD 10 via a data/address bus 55. IMD 10 includes therapy delivery module 50 for delivering a therapy in response to determining a need for the therapy based on sensed physiological signals. Therapy delivery module 50 may provide drug delivery therapies or electrical stimulation therapies, such as cardiac pacing or anti-arrhythmia therapies. Therapies are delivered by module 50 under the control of timing and control 52. Therapy delivery module 50 is typically coupled to two or more electrode terminals 68 via an optional switch matrix 58 for delivering electrical stimulation therapies. Switch matrix 58 may be used for selecting which electrodes and corresponding polarities are used for delivering electrical stimulation pulses. Terminals 68 may be coupled to connectors providing electrical connection to electrodes incorporated along housing 12 or other lead-based electrodes.

Electrode terminals 68 can also used for receiving electrical signals, such as cardiac signals. Cardiac electrical signals may be monitored for use in diagnosing or monitoring a patient condition or may be used for determining when a therapy is needed and in controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias, detecting hemodynamic events, syncope, or other patient conditions.

IMD 10 may additionally be coupled to one or more physiological sensors via physiological sensor terminals 70. Physiological sensors may include pressure sensors, accelerometers, flow sensors, blood chemistry sensors, activity sensors or other physiological sensors known for use with implantable devices. Physiological sensors may be carried by leads extending from IMD 10 or incorporated in or on the IMD housing 12. Signals received at sensor terminals 70 are received by a sensor interface 62, which may filter, amplify, rectify or otherwise condition a received signal prior to inputting sensor signals to signal processing circuitry 60. Sensor signals are processed by processing circuitry 60 and/or microprocessor 54 for detecting physiological events or conditions.

IMD 10 includes an acoustic element 40 shown coupled to acoustic sensing/alert circuitry 20. In one embodiment, acoustic element 40 is a piezoelectric transducer deployed along an inner surface of IMD housing 12. Acoustic element 40 is implemented as a dual function element being responsive to physiological sounds for use as an acoustical sensor as well as being responsive to an alert driver signal for use in generating an audible patient alert. As will be described herein, sensing/alert circuitry 20 controls the function of element 40 as either a sensor or an alert and provides the unique frequency and other operation characteristics for a sensing circuitry pathway and for an alert circuitry pathway, each utilizing the common acoustic element 40.

When functioning as a sensor, physiological sounds, such as heart sounds, lung sounds, or intestinal sounds are received by element 40 and an electrical signal is generated by element 40 and received by sensing/alert circuitry 20. As such, element 40 may be designed and positioned along IMD housing 12 to be sensitive to physiological sounds in the range of about 15 Hz to 400 Hz generally corresponds to heart sound frequencies, about 600 Hz to about 2000 Hz generally corresponding to lung sound frequencies, or up to about 300 Hz generally corresponding to intestinal sound frequencies. When implemented as an acoustical sensor for monitoring physiological sounds, low frequency signals, for example less than about 10 Hz, which correspond to physical activity of the patient are generally filtered, either mechanically or electrically.

When functioning as a patient alert, sensing/alert circuitry 20 generates a patient alert drive signal that activates element 40 to cause IMD housing 12 to resonate. The drive signal may be selected to be at or near the resonant frequency of the IMD housing 12 at the location of element 40. The drive signal may alternatively be selected based on the auditory acuity of the patient such that the frequency of the IMD housing vibration corresponds to a tone audible to the patient, which may or may not be the natural resonant frequency of the IMD housing 12.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Algorithms may be stored in memory 56 and executed by microprocessor 54 for determining alert conditions which trigger alert/sensing circuitry 20 to generate an alert drive signal and switch the operation of acoustic element 40 from a sensing function to an alert function. A patient alert may be triggered in response to detecting a physiological event or condition using any sensors coupled to terminals 70 as well as acoustic signals sensed using acoustic element 40. Patient alert conditions may alternatively or additionally relate to IMD functions or status. Data relating to patient alert signals as well as acoustical signals sensed by element 40 and alert signal delivered by element 40 may be stored in memory 56 for later retrieval.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit. Telemetry circuitry 64 and antenna 65 may correspond to telemetry systems known in the art.

Figure 2:
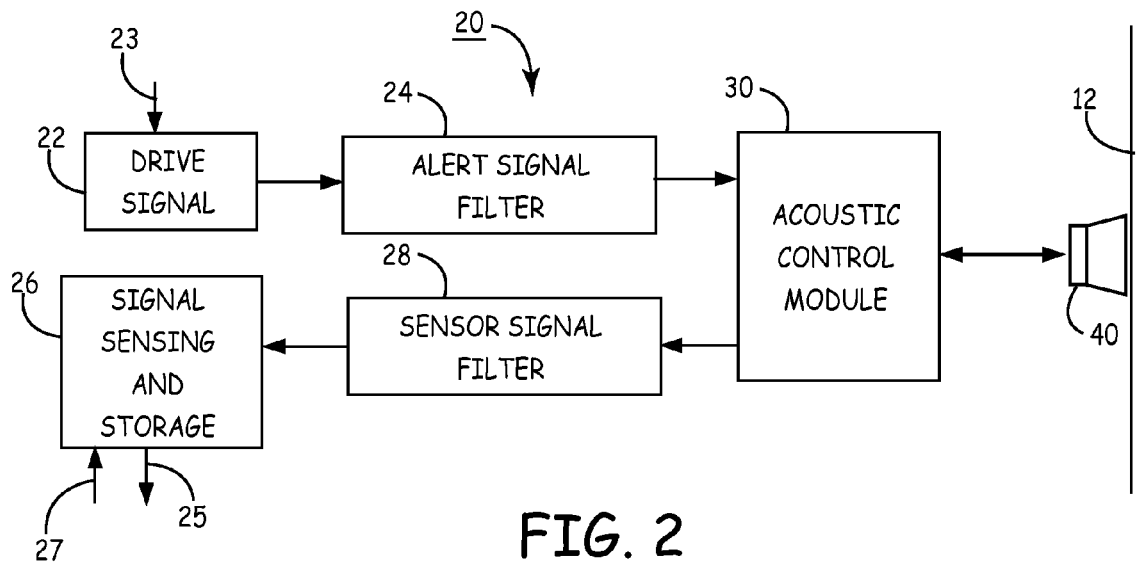
FIG. 2 is a functional block diagram of circuitry used for controlling the dual functions of an acoustic element operating as a sensor and as an alert signal generator.

FIG. 2 is a functional block diagram of circuitry used for controlling the dual functions of an acoustic element operating as a sensor and as an alert signal generator. A drive signal module 22 receives input 23 from the IMD microprocessor or other control circuitry indicating a condition has been detected requiring a patient alert. Input signal 23 causes drive signal module 22 to generate a drive signal having a desired alert signal frequency and amplification, for example using push/pull amplification, for activating acoustic element 40. The drive signal is received by the alert signal filter 24 for filtering to achieve a desired drive signal frequency for causing the housing 12 to resonate. In one embodiment, the filtered frequency is selected to optimize the sympathetic response of the housing 12 to vibrate at its natural resonant frequency. The natural resonant frequency will depend on the material properties, such as material type, thickness, etc., as well as the location of the acoustic element 40 on the housing relative to the stress/strain properties of the housing configuration, the arrangement of components within the housing, and so on.

Acoustic control module 30 detects the presence of the alert signal and responds by isolating the sensor pathway, which includes sensor signal filter 28 and sensing and storage module 26, from acoustic element 40. Acoustic control module 30 couples the alert driver signal to element 40 to cause activation of element 40 and, in turn, resonance of housing 12. In this way, an acoustical alert signal is generated that is perceivable by the patient. Prior to detecting the presence of the alert driver signal, acoustic control module 30 may decouple element 40 from the alert pathway, including alert signal filter 24 and drive signal module 22.

The sensor pathway, including filter 28 and sensing and storage module 26, is designed to be sensitive to lower amplitude and lower frequency signals than the acoustic alert signal. As such, to prevent sensor signal corruption, saturation of sense amplifiers, and potential damage to circuitry in the sensing pathway, the acoustic control module 30 electrically isolates the acoustic element 40 from filter 28 in the presence of an alert drive signal. Isolation circuitry may be in the form of a switch, multiplexer, or other logic circuitry implemented to electrically decouple filter 28 from acoustic element 40. Acoustic control module 30 may also decouple the alert pathway, including alert signal filter 24 and drive signal module 22, from acoustic element 40 when an alert signal is not being received from alert signal filter 24.

Sensor signal filter 28 is designed to pass physiological signals of interest and will vary between embodiments according to the needs of a particular application. In one embodiment filter 28 is implemented as a resistor for filtering high frequency signals and passing low frequency signals, for example on the order of 15 to 400 Hz, characteristic of physiological signals such as heart sounds. Filter 28 may be implemented for filtering multiple signal frequencies or frequency ranges to allow monitoring of physiological signals having different frequency characteristics, for example as a multi-channel system.

Signal sensing and storage module 26 receives the filtered signal(s) and detects acoustic events, for example using a sense amplifier with threshold-crossing detection. Sensing and storage module 26 may include multiple channels for sensing differently filtered acoustic signals from filter 28. Signal sensing and storage module 26 may further include dedicated memory for storing signal data or may provide signal data to IMD memory, the IMD microprocessor or other control circuitry via output line 25. A sensed event signal may be provided on output line 25 for use by the IMD microprocessor in detecting a physiological condition or event. In one embodiment, signal sensing and storage module 26 senses heart sounds for use in monitoring cardiac function, such as evaluating heart rhythms or detecting hemodynamic events.

When an alert drive signal is not present, acoustic control module 30 maintains electrical connection between acoustic element 40 and filter 28 such that the sensing pathway is operational for sensing acoustic signals. Signal sensing and storage module 26 may be active or inactive according to an input control signal 27. Input control signal 27 may be generated by the IMD microprocessor or other control circuitry for enabling signal sensing and storage module 26 to acquire acoustical data during periods of interest. In other words, when the alert drive signal is not present, acoustic sensing may occur on a triggered or scheduled basis rather than on a continuous basis depending on the sensing and power-savings requirements of the particular IMD. Input signal 27 may alternatively be received by acoustic control module 30 such that acoustic control module 30 couples element 40 to the sensor signal filter 28 only as needed during triggered or scheduled sensing episodes. Acoustic control module 30 may also provide filter 28 with control signals for selecting the filtering characteristics, or multiplexing different filtering channels, of filter 28 as appropriate for the signal being sensed.

Figure 3:
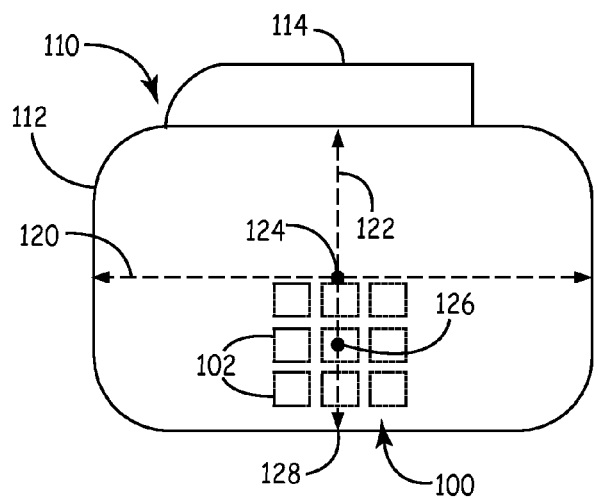
FIG. 3 is a schematic diagram of an acoustic element embodied as an array of elements deployed along an IMD housing.

FIG. 3 is a schematic diagram of an acoustic element embodied as an array of elements deployed along an IMD housing. IMD 110 includes housing 112 for enclosing IMD circuitry (not shown) and a connector 114 for receiving leads extending from IMD 110. In one embodiment, a dual function acoustic element is embodied as an array 100 of individual piezoelectric elements 102 positioned along an interior surface of IMD housing 112. Piezoelectric elements may be positioned in a regular geometric pattern, such as the 3×3, linearly aligned array shown in FIG. 3, or any non-linear, staggered, irregular or random pattern, including any number of elements.

The operational requirements of a piezoelectric element for causing IMD housing 112 to resonate and the operational requirements for a piezoelectric element for sensing physiological signals are very different and have thus resulted in acoustic elements implemented separately for each function, as a sensor or as an alarm but not both. Implementation of a dual function acoustic element as described above allows IMD size and cost reduction and simplification of manufacturing processes. By implementing a dual function acoustic element as an array of elements, the behavior of the acoustic element can be optimized for each of the two separate functions.

Elements of array 100 may be configured along a surface of housing 12 in a pattern or arrangement that allows the resonance of housing 12 to be maximized for audible perception by a patient. In one embodiment, the array 100 is centered along a long axis 120 of a major side and on a midway point 126 between the center 124 of a short axis 122 and an outer edge 128 of housing 112. Vibration of housing 112 at its natural resonant frequency in response to an appropriately tuned drive signal is expected to be maximized at this midway point 126. It is recognized, however, that the optimal position of an acoustic element or combination of elements within an array for generating a perceptible patient alert signal will vary between embodiments.

Since the optimal location of one or more elements used for generating an alert signal may be different than the optimal location of elements used for sensing, the array 100 is configured to allow selection of different elements at different locations for performing sensing and alert functions. While array 100 is shown having elements positioned along one interior major surface of housing 112, an array including elements along one or more major and/or minor surface is not beyond the scope of embodiments of the present invention.

Figure 4:
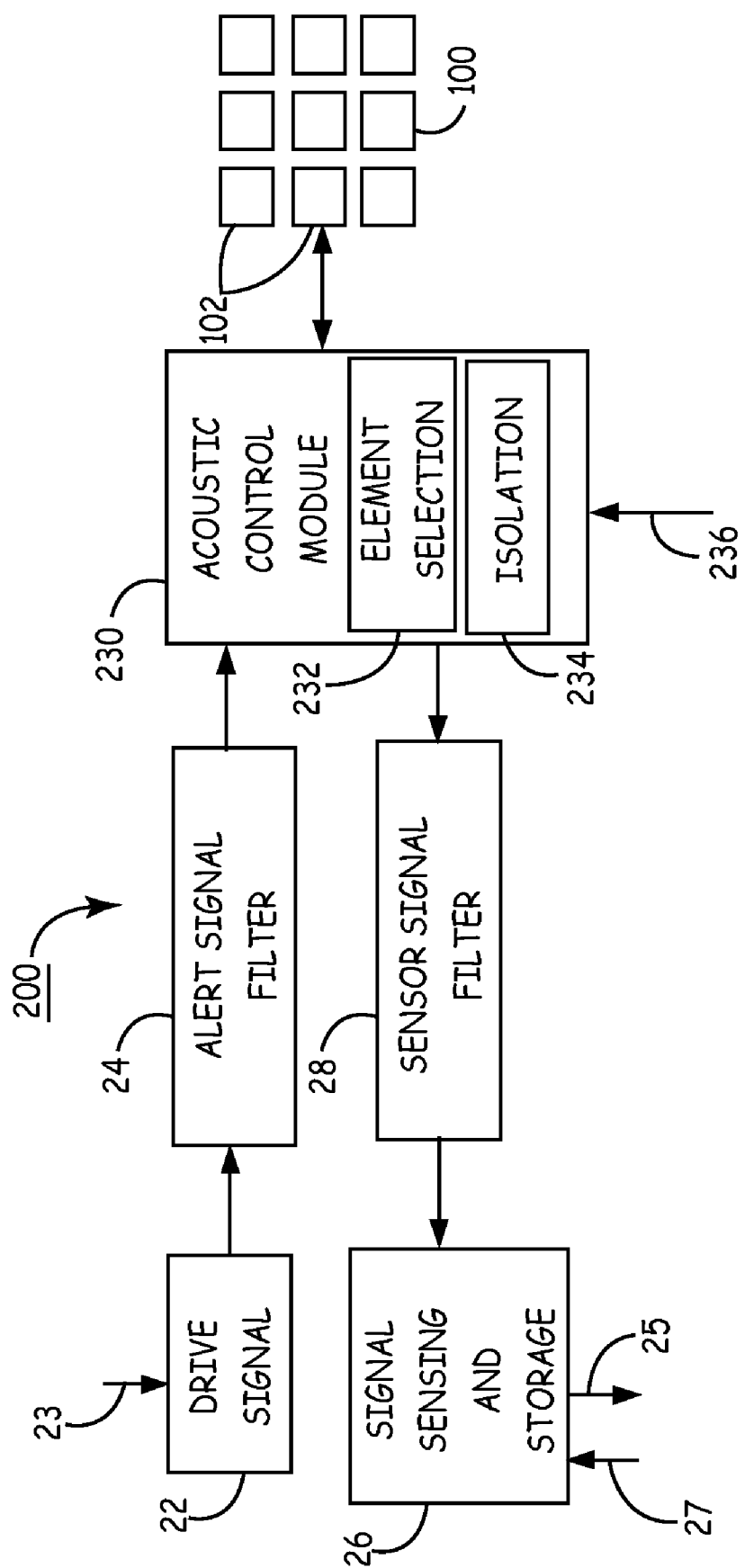
FIG. 4 is a functional block diagram of acoustical alert and sensing circuitry for use with a dual function acoustic element array.

FIG. 4 is a functional block diagram of acoustic alert and sensing circuitry 200 for use with a dual function acoustic element array 100. Drive signal module 22 having input signal 23 and alert signal filter 24 generally operate in the manner described previously. Likewise, signal sensing and storage module 26 having output 25 and input 27 and sensor signal filter 28 generally operate in the manner described above. Acoustic control module 230 includes isolation circuitry 234 for electrically isolating the sensor pathway, i.e. filter 28 and sensing and storage module 26, from acoustic element array 100 when an alert drive signal is present. Isolation circuitry 234 may include a switch, resistor, multiplexer or other circuitry for electrically isolating filter 28 from array 100.

When an alert drive signal is not present, array 100 is electrically coupled to filter 28 and sensing and storage module 26 via acoustic control module 230. Acoustic control module 230 includes element selection circuitry 232 for selecting which elements 102 of array 100 are coupled to filter 28 when a drive signal is not present. The elements 102 that are selected may be preprogrammed or selected via logic operations performed by element selection 232 or based on an input signal 236 received from the IMD microprocessor or other control circuitry. The elements 102 that are selected for sensing may be optimized for the best signal-to-noise ratio and/or highest sensitivity to the physiological sounds of interest. When more than one physiological signal is monitored, different elements may be selected based on the signal being sensed. For example, one set of elements including one or more of elements 102 may be selected for sensing one heart sound and a different set of elements may be selected for sensing a different heart sound. Alternatively, one set of elements may be selected for sensing heart sounds and a different set of elements may be selected for sensing respiratory sounds.

Element selection for sensing may be based on which elements provide the optimal signal for sensing a desired physiological sound. Furthermore, if the signal-to-noise ratio worsens or the signal quality is otherwise suspected to have worsened or become corrupted, different elements may be selected to find a better sensing configuration.

Element selection 232 is further configured to select which elements 102 of array 100 are activated by the drive signal for emitting a patient alert. Element selection for the patient alert function may be preprogrammed or based on control signals received on input 236 or based on the frequency, voltage or other characteristics of the alert drive signal received from drive signal generator 22 and filter 24. Furthermore, different elements or combinations of elements may be selected in sequence to create a patterned or multi-tone alert. Different "ring tones" may be implemented by sequential selection of different elements 102 or combinations of elements 102 to communicate to the patient the type of alert condition detected or the type of response to be taken based on the audible alert pattern.

Figure 5:
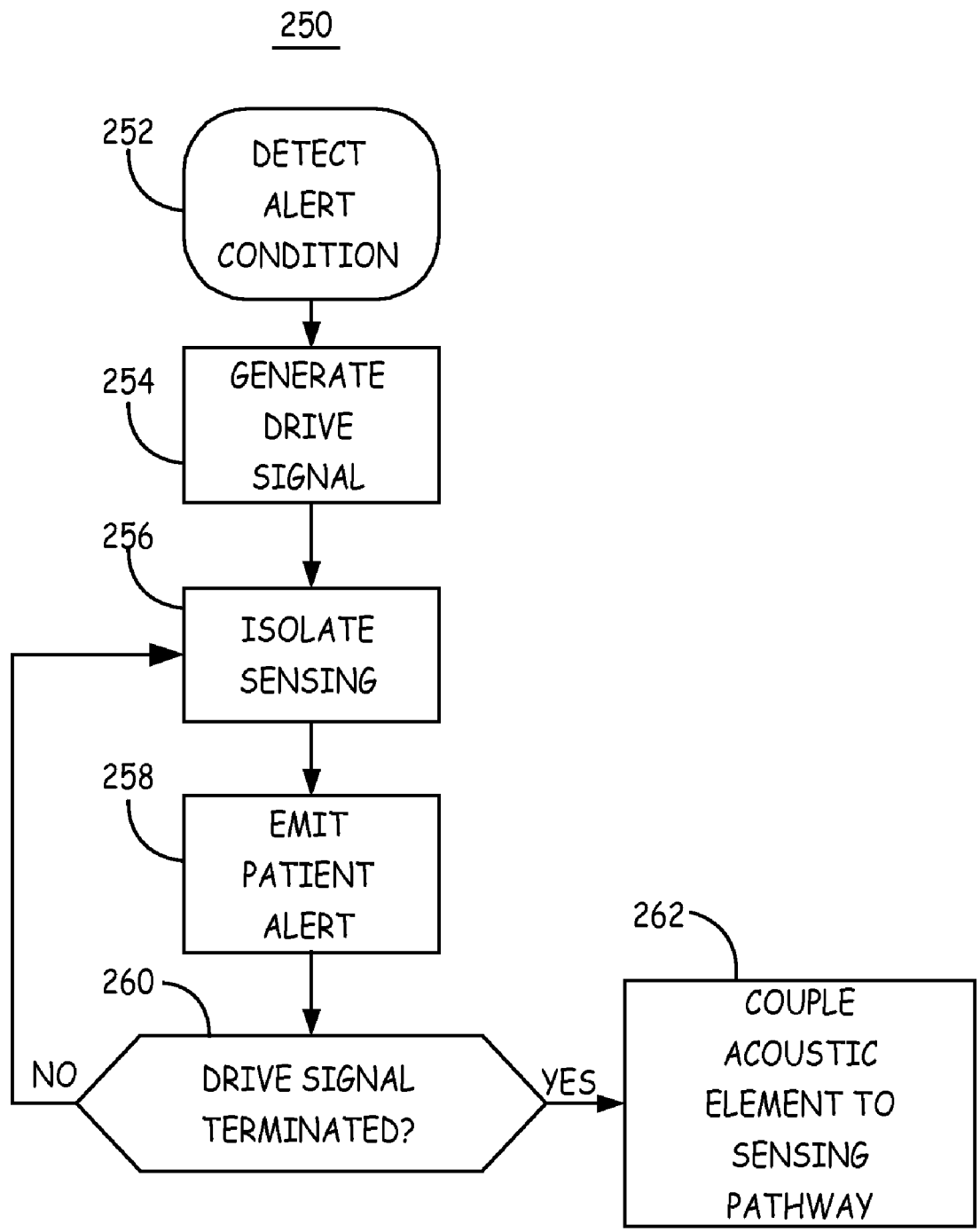
FIG. 5 is a flow chart of a method for controlling a dual function acoustic element.

FIG. 5 is a flow chart of a method for controlling a dual function acoustic element. Flow chart 250 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 252, an alert condition is detected by the IMD. An alert drive signal is generated in response to the detected alert condition at block 254. An acoustical sensing pathway is isolated from an acoustic element at block 256 in response to the alert drive signal. If not already coupled to the acoustic element, an acoustical patient alert pathway is coupled to the acoustic element in response to the drive signal. An alert signal is emitted by the acoustic element at block 258. When the alert drive signal is terminated, as determined at block 260, the acoustical sensing pathway is electrically coupled to the acoustic element at block 262 to enable acoustic sensing using the acoustic element.

Thus, apparatus and methods for implementing a dual function acoustic element have been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
   an acoustic element;
   a control module coupled to the acoustic element for controlling the function of the acoustic element;
   an acoustic sensing module coupled to the control module for receiving acoustical signals from the acoustic element via the control module;
   a patient alert driver module coupled to the control module and generating a patient alert drive signal for activating the acoustic element via the control module to emit a patient alert signal; and
   an alert filter coupled to the patient alert driver module and the control module for passing a selected alert signal frequency to the control module;
   the control module configured to detect the patient alert drive signal and comprising an isolation circuit for isolating the acoustic sensing module from the acoustic element in response to the patient alert drive signal.

2. An implantable medical device, comprising:
   an acoustic element;
   a control module coupled to the acoustic element for controlling the function of the acoustic element;
   an acoustic sensing module coupled to the control module for receiving acoustical signals from the acoustic element via the control module;
   a patient alert driver module coupled to the control module and generating a patient alert drive signal for activating the acoustic element via the control module to emit a patient alert signal; and
   a sensing filter for receiving an acoustical signal from the control module and passing a selected sensing signal frequency to the acoustic sensing module;
   the control module configured to detect the patient alert drive signal and comprising an isolation circuit for isolating the acoustic sensing module from the acoustic element in response to the patient alert drive signal.

3. The device of claim 1, wherein the acoustic element comprises a piezoelectric element.

4. The device of claim 3, further comprising a housing for enclosing the control module, the acoustic sensing module, and the patient alert driver module, the piezoelectric element being positioned along an interior surface of the housing.

5. The device of claim 4, wherein the acoustic element comprises an array of piezoelectric elements distributed along the interior surface of the housing.

6. An implantable medical device, comprising:
   an acoustic element, wherein the acoustic element comprises a piezoelectric element;
   a control module coupled to the acoustic element for controlling the function of the acoustic element;
   an acoustic sensing module coupled to the control module for receiving acoustical signals from the acoustic element via the control module;
   a patient alert driver module coupled to the control module and generating a patient alert drive signal for activating the acoustic element via the control module to emit a patient alert signal; and
   a housing for enclosing the control module, the acoustic sensing module, and the patient alert driver module, the piezoelectric element being positioned along an interior surface of the housing;
   the control module configured to detect the patient alert drive signal and comprising an isolation circuit for isolating the acoustic sensing module from the acoustic element in response to the patient alert drive signal, wherein the acoustic element comprises an array of piezoelectric elements distributed along the interior surface of the housing, and wherein the control module further comprises selection circuitry configured to activate selected ones of the array of piezoelectric elements for emitting a patient alert signal.

7. An implantable medical device, comprising:
   an acoustic element, wherein the acoustic element comprises a piezoelectric element;
   a control module coupled to the acoustic element for controlling the function of the acoustic element;
   an acoustic sensing module coupled to the control module for receiving acoustical signals from the acoustic element via the control module;
   a patient alert driver module coupled to the control module and generating a patient alert drive signal for activating the acoustic element via the control module to emit a patient alert signal; and
   a housing for enclosing the control module, the acoustic sensing module, and the patient alert driver module, the piezoelectric element being positioned along an interior surface of the housing;
   the control module configured to detect the patient alert drive signal and comprising an isolation circuit for isolating the acoustic sensing module from the acoustic element in response to the patient alert drive signal, wherein the acoustic element comprises an array of piezoelectric elements distributed along the interior surface of the housing, and wherein the control module further comprises selection circuitry configured to couple selected ones of the array of piezoelectric element to the sensing module.

8. A method for controlling an acoustic element in an implantable medical device, comprising:
   detecting a patient alert condition;
   generating a patient alert drive signal;
   isolating an acoustic sensing module from an acoustic element in response to the patient alert drive signal; and
   activating the acoustic element to emit a patient alert signal in response to the patient alert drive signal, wherein the acoustic element comprises an array of piezoelectric elements and further comprising:
     selecting a first set of the piezoelectric elements to receive the patient alert drive signal in response to the patient alert drive signal being generated;
     detecting termination of the patient alert drive signal; and
     coupling a second set of the piezoelectric elements, different than the first set, to the acoustic sensing module in response to detecting termination of the patient alert drive signal.

* * * * *